(12) United States Patent (10) Patent No.: US 12,611,210 B1
Cichocki et al. (45) Date of Patent: Apr. 28, 2026

(54) METHOD AND SYSTEM FOR MANUFACTURING A BARBED SUTURE

(71) Applicant: ETHICON, INC., Raritan, NJ (US)

(72) Inventors: Frank Cichocki, Raritan, NJ (US); Duru Han, Raritan, NJ (US); Robert Scogna, Raritan, NJ (US)

(73) Assignee: Ethicon, Inc., Raritan, NJ (US)

( * ) Notice: Subject to any disclaimer, the term of this patent is extended or adjusted under 35 U.S.C. 154(b) by 0 days.

(21) Appl. No.: 19/262,812

(22) Filed: Jul. 8, 2025

(51) Int. Cl.
　　*A61B 17/06* 　　　(2006.01)
　　*A61B 17/00* 　　　(2006.01)
(52) U.S. Cl.
　　CPC ............... *A61B 17/06166* (2013.01); *A61B 2017/00526* (2013.01); *A61B 2017/00884* (2013.01); *A61B 2017/06176* (2013.01)
(58) Field of Classification Search
　　CPC ............. A61B 17/06; A61B 17/06166; A61B 2017/00526; A61B 2017/00884; A61B 2017/06176; C22F 1/16
　　See application file for complete search history.

(56) References Cited

U.S. PATENT DOCUMENTS

| | | | | |
|---|---|---|---|---|
| 4,989,439 | A | * | 2/1991 | Ewert .................... B21D 25/02 |
| | | | | 72/702 |
| 5,676,008 | A | * | 10/1997 | Morin ..................... B21F 11/00 |
| | | | | 83/907 |
| 2009/0157117 | A1 | * | 6/2009 | Reynolds ................. B21G 1/08 |
| | | | | 420/432 |

* cited by examiner

*Primary Examiner* — Vi X Nguyen
(74) *Attorney, Agent, or Firm* — Amir Bishara

(57) ABSTRACT

A method for manufacturing a monofilament barbed suture. The method includes positioning a mandrel device adjacent to a rotary mount on which a razor is mounted, the mandrel device comprising a mandrel mounted to a fixture, a filament in contact with a curved surface of the mandrel; and rotating the razor with the rotary mount so that an edge of the razor impinges upon an exterior surface of the filament to impart a linear cut to the filament to a cut depth within the filament to form a barb. The mandrel has a diameter of 4 millimeters or less.

14 Claims, 7 Drawing Sheets

SYSTEM 100

102

104

SYSTEM 100

102

104

110

113

108

112

SYSTEM 200

204

202

213

212

210

206

208

SYSTEM 200

METHOD AND SYSTEM FOR MANUFACTURING A BARBED SUTURE

BACKGROUND

Barbed sutures include a plurality of barbs extending radially away from the surface of a filament. These sutures can eliminate the need for knots by providing an anchoring force along the length of the suture, e.g., helping to prevent the suture from slipping out of the tissue as the barbs penetrate the tissue adjacent to the suture.

SUMMARY

The present disclosure relates to a system for manufacturing a monofilament barbed suture. The system includes a rotary mount configured to rotate about a central axis; a razor mounted to the rotary mount; and a mandrel device positioned adjacent to the rotary mount, the mandrel device comprising a mandrel mounted to a fixture, the mandrel configured to support a filament on a curved surface of the mandrel so that, as the razor rotates with the rotary mount, an edge of the razor impinges upon an exterior surface of the filament to impart a linear cut to the filament to a cut depth within the filament to form a barb. The mandrel comprises a diameter of 4 millimeters or less.

In an embodiment, the curved surface of the mandrel having the diameter of 4 millimeters or less is configured to impart a curvature to the filament so that the linear cut into the filament by the razor results in a cut surface of the filament that, upon transitioning off the curved surface of the mandrel, exhibits a continuous curve, the cut surface extending from a first end at the exterior surface of the filament to a second end at the cut depth. A first angle of a first tangent of the cut surface at the first end is greater than a second angle of a second tangent of the cut surface at the second end relative to a longitudinal axis of the filament.

In an embodiment, the mandrel device is oriented so that a cut path of the razor imparts the linear cut into the filament such that the first angle of the first tangent of the cut surface at the first end is greater than 15 degrees relative to the longitudinal axis of the filament.

In an embodiment, the mandrel device is oriented so that the cut path of the razor imparts the linear cut into the filament such that the second angle of the second tangent of the cut surface at the second end, upon transitioning off the curved surface of the mandrel, is less than 5 degrees.

In an embodiment, the system further includes a filament control system to which a first end of the filament upstream from the mandrel and a second end of the filament downstream from the mandrel are coupled. The filament control system is configured to pull the first end of the filament and the second end of the filament to provide axial tension to the filament. The axial tension brings the filament into contact with the curved surface of the mandrel.

In an embodiment, the filament control system includes a spool around which the filament is wound and a braking system imparting the axial tension to the filament, wherein the spool is rotated to wind the filament and translate the filament along the curved surface of the mandrel so that, upon a subsequent rotation of the razor around the rotary mount, a further linear cut is imparted to a portion of the filament adjacent to the linear cut.

In an embodiment, the rotary mount rotates at a set velocity and the filament control system translates the filament along the curved surface of the mandrel a predetermined distance per rotation of the rotary mount to form a series of barbs along a length of the filament.

In an embodiment, translating the filament along the curved surface of the mandrel is performed continuously while the series of barbs is formed.

In an embodiment, translating the filament along the curved surface of the mandrel is performed in steps and, during each linear cut, the filament is not translating along the curved surface of the mandrel.

In an embodiment, the fixture of the mandrel device includes a first surface against which a first portion of the filament upstream from the linear cut is held and a second surface against which a second portion of the filament downstream from the linear cut is held, the first and second surfaces providing forces to impede uncontrolled motion of the filament during barb cutting.

In an embodiment, the system further includes a mechanical barb lifter mounted to the rotary mount. The barb lifter is configured to rotate with the rotary mount to impinge upon a cut side of the barb to increase a height of the barb relative to the filament. The barb lifter impinging upon the cut side of the barb plastically deforms the barb so that the height of the barb is maintained.

In an embodiment, the razor is mounted to the rotary mount at a first position opposing a second position of the barb lifter.

In an embodiment, the system further includes a heat source configured to provide a set temperature to a cut barb for a set duration to cause the barb to deflect radially outwards to increase a height of the barb relative to the filament.

In an embodiment, the heat source is configured to be applied when the filament is under axial tension.

In an embodiment, a ratio of mandrel diameter to filament diameter is greater than 3 and less than 25.

In addition, the present disclosure relates to a method for manufacturing a monofilament barbed suture. The method includes positioning a mandrel device adjacent to a rotary mount on which a razor is mounted, the mandrel device comprising a mandrel mounted to a fixture, a filament in contact with a curved surface of the mandrel; and rotating the razor with the rotary mount so that an edge of the razor impinges upon an exterior surface of the filament to impart a linear cut to the filament to a cut depth within the filament to form a barb. The mandrel comprises a diameter of 4 millimeters or less.

In an embodiment, the curved surface of the mandrel having the diameter of 4 millimeters or less is configured to impart a curvature to the filament so that the linear cut into the filament by the razor results in a cut surface of the filament that, upon transitioning off the curved surface of the mandrel, exhibits a continuous curve, the cut surface extending from a first end at the exterior surface of the filament to a second end at the cut depth. A first angle of a first tangent of the cut surface at the first end is greater than a second angle of a second tangent of the cut surface at the second end relative to a longitudinal axis of the filament.

In an embodiment, the method further includes providing axial tension to the filament to bring the filament into contact with the curved surface of the mandrel by pulling a first end of the filament upstream from the mandrel and pulling a second end of the filament downstream from the mandrel by a filament control system to which the first end and the second end are coupled; and translating the filament along the curved surface of the mandrel by rotating a spool around which the filament is wound while imparting the axial tension to the filament by a braking system so that, upon a subsequent rotation of the razor around the rotary mount, a further linear cut is imparted to a portion of the filament adjacent to the linear cut.

In an embodiment, the method further includes rotating a mechanical barb lifter mounted to the rotary mount with the rotary mount to impinge upon a cut side of the barb to increase a height of the barb relative to the filament, the barb lifter plastically deforming the barb so that the height of the barb is maintained.

In an embodiment, the method further includes imparting, by a heat source, a set temperature to a cut barb for a set duration to cause the barb to deflect radially outwards to increase a height of the barb relative to the filament.

DETAILED DESCRIPTION

Figure 1:
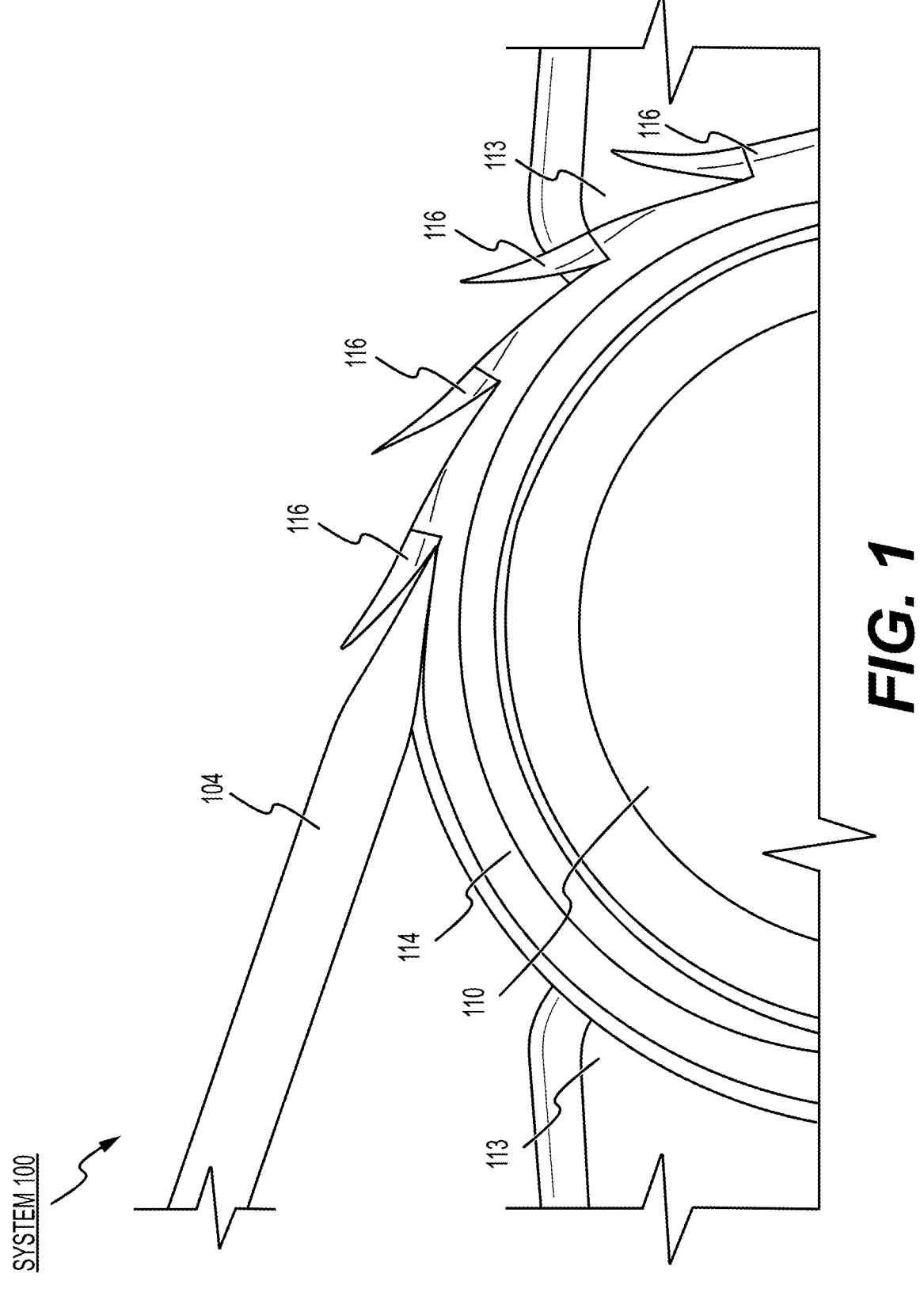
FIG. 1 shows a system including a razor striking a suture filament curved around a mandrel to form barbs according to various exemplary embodiments.

The exemplary embodiments may be further understood with reference to the following description and the appended drawings, wherein like elements are referred to with the same reference numerals. The exemplary embodiments relate to systems and methods for manufacturing barbed sutures, in particular, barbed sutures having elongate barbs formed at a modest cut depth into the filament of the suture.

Barbed sutures offer a variety of potential benefits. In one example, barbed sutures can speed up and/or simplify the tissue closure process by eliminating the need for knots to secure the sutures while freeing up one of the surgeon's hands which may otherwise be required to maintain tension on the suture during wound closure. In another example, barbed sutures can achieve superior intimate tissue contact between the tissues spanning an incision, anastomosis or other tissue opening to be closed while offering a wound holding strength stronger than that attainable with conventional sutures, e.g., using standard continuous suturing techniques. In still another example, barbed sutures can allow for easy passage through tissue in one direction, e.g., a direction in which a suture is to be passed through the tissue during application of the suture. These potential benefits are generally dependent on barb design.

The barb design includes attributes or properties such as a barb length, a barb shape, and a general pattern distribution of barbs along the length and around the circumference of the suture, e.g., sequential barbs formed along a linear path, along a curved path (i.e., an arcuate, spiral or helical path), etc. Various barb designs are currently commercially available with each of these barb designs exhibiting different suture properties.

Some barbed sutures are manufactured by, for example, razor cutting a filament. The razor cutting technique generally comprises mounting the filament around a large diameter mandrel (e.g., ~25 mm diameter) and applying controlled cuts to the outer surface of the filament at one or more predetermined cut angles relative to the outer surface of the filament (i.e., relative to a line or plane tangent to the outer surface of the filament and/or parallel to the longitudinal axis of the filament). Each of these cuts is applied to a desired depth into the filament to separate the material that will form the barbs from adjacent parts of the suture, and this material is then extended at an angle radially away from filament to form barbs.

As understood by those skilled in the art, the filament can be passed along the mandrel so that the razor sequentially cuts the filament to form a series of barbs. This process often results in relatively short barbs that extend away from the filament at a relatively small angle. Other barbed sutures have been manufactured using a compound cut process in which a first cut is made at a first angle relative to the filament and a second cut is then made at a second angle relative to the filament. Still other barbed sutures have been manufactured using a die cutting process applied to a pre-formed filament.

Each of the example sutures described above has various benefits and detriments. For example, manufacturing a barbed suture by forming each barb via a single razor cut is a relatively simple process when short barbs are desired. However, these short barbs have a relatively low tissue holding strength. In another example, although forming barbs using compound cuts is more complicated than the process for forming single cut barbed sutures, these compound cut sutures have increased barb height and improved first pass holding strength as compared to the short barb sutures.

Both types of razor cut barbed sutures described above exhibit relatively low passage forces due in part to the ability of the barbs to fold back against the body of the suture (into the space this material occupied before the barbs were cut) during tissue passage. Furthermore, sutures having barbs formed by die cutting often exhibit increased barb height and tissue holding strength as compared to single and compound cut sutures. However, these die-cut barbed sutures often exhibit poorer tissue passage properties relative to the preceding razor cut barb designs due in part to the inability of the barbs to fold back against the body of the suture during tissue passage as effectively as the razor cut barbs. This impedes the passage of these die cut sutures through tissue as would be understood by those skilled in the art.

According to various exemplary embodiments described herein, a barbed suture is formed at least in part by a razor cutting process in which a filament is curved around a small diameter mandrel, such that a straight razor cut to the filament (i.e., a razor cut along a linear cut path) enters the curved filament at a first angle (relative to a longitudinal axis of the filament) and follows a path through the filament that terminates substantially parallel to the longitudinal axis of the filament. Although the actual razor cut is a straight cut (in space), when the filament is straightened into a linear form (or a less curved form), the resulting shape of the cut within the filament is curved relative to the longitudinal axis of the filament. This permits the formation of long barbs without deep penetration of the razor into the thickness of the filament.

Compared to existing razor cut barbed sutures, the barbs according to the present embodiments may be significantly longer, e.g., exhibiting a higher ratio of barb height to filament diameter, as described in greater detail below. The exemplary manufacturing processes described herein can produce long barbs at a modest cross-sectional cut depth, thereby minimizing the impact of the barb cutting process on the tensile strength of the suture.

The razor cutting process used to produce the barbed sutures according to the present disclosure differs from conventional razor cutting processes in several significant ways. The first major difference is associated with the diameter of the mandrel around which the suture filament is wrapped during the cutting process. In some embodiments, a mandrel diameter of ~1.5 to 4 mm can be used, whereas, in the conventional razor cut barbing process, a mandrel diameter of ~25 mm is typically used. The fine diameter mandrel imparts a tighter curvature to the suture filament that enables the razor to strike the outside of the suture filament at a significant angle (e.g., greater than 15 degrees), providing structural integrity to the tip of the barb, while finishing the cut inside the suture filament at an angle approaching, equal to, or greater than zero degrees with respect to the filament axis.

In an exemplary embodiment, a ratio of the mandrel diameter to the suture filament diameter is preferably less than 25. Practically speaking, in exemplary embodiments, mandrel diameter-to-suture diameter ratios of greater than 3 are used to ease manufacturing set up and control. The elongate barb shape can also be advantageous in achieving suture strength since the finish angle of the cut is oriented predominantly along the filament axis as opposed to at a steeper angle to the filament axis as seen in conventional short cut barbed sutures. By minimizing cut depth and finishing cut angle, a majority of the filament cross-section remains intact resulting in a high retained tensile strength.

FIG. 1 shows a system 100 including a razor 104 striking a suture filament 114 curved around a mandrel 110 to form barbs 116 according to various exemplary embodiments. As shown, the razor 104 slices into the suture filament 114 at a fixed angle with respect to the tangent of the suture filament 114 at the point of impingement and produces a straight cut through the tightly wrapped suture filament 114 until the razor 104 is approximately parallel with the filament axis. In other words, the straight cut enters the curved suture filament 114 at a certain angle (at least 15 degrees, e.g., 20 degrees) relative to the longitudinal axis (or the tangent of the outer surface) of the suture filament 114 at the point of impingement and finishes at a different angle relative to the longitudinal axis at the end of the cut. In some embodiments, the cut is finished at an angle (an angle of a tangent to the cut surface at the end of the cut) approaching zero degrees (or equal to zero degrees or even falling below zero degrees) with respect to the longitudinal axis of the suture filament 114. In some embodiments, the cut is finished at an angle (an angle of a tangent to the cut surface at the end of the cut) less than 5 degrees.

Although the pathway of the cut is linear in space as the cut strikes through the suture filament 114 (while the suture filament 114 is tightly wrapped around the mandrel 110), as the cut portion (barb 116) of the suture filament 114 is drawn off the mandrel (or when the suture is removed entirely from the mandrel) and the filament straightens, the cut path through the filament extends along a continuous curve within the filament.

It is noted that FIG. 1 additionally shows surfaces 113 of a fixture 112 on which the mandrel 110 is mounted. The suture filament 114 is held against these surfaces 113 during the manufacturing process, in particular, a portion of the suture filament 114 upstream of the cut location and a portion of the suture filament 114 downstream of the cut location are held against respective surfaces 113 so that the suture filament 114 does not deviate from its path as it travels around the mandrel 110. These surfaces can help to impede undesirable motion of the filament during the barb cutting process. The process for manufacturing the exemplary barbed sutures comprises a carefully controlled process for imparting precision cuts to the suture filament 114 to create a series of barbs along a length of the suture filament 114, as will be described in greater detail below.

In some aspects of the present disclosure, a system for manufacturing a barbed suture comprises a rotary mount and a razor mounted thereon for cutting barbs into a monofilament suture. The razor can be mounted at a location on the rotary mount (e.g., a radial distance away from the center of the mount) so that rotating the rotary mount correspondingly rotates the razor along a controlled path, e.g., a cut path. The system further includes a mandrel device including a fixture and a mandrel mounted thereon. The mandrel can comprise a cylindrical rod, e.g., a dowel pin. The system further includes devices for holding the ends of the filament, e.g., a tension control system comprising respective spools around which the filament can be partially wrapped or unwrapped. The filament is partially wrapped around the mandrel, e.g., a 180-degree curve with the ends of the filament held by a device (e.g., spool) (or a respective device for holding each end), to provide tension and advance the filament around the mandrel so that the razor can sequentially impart a series of cuts along a length of the filament.

These components are carefully positioned, oriented and controlled so that the edge of the razor can impart a linear cut to the filament as it travels around the rotary mount to achieve a selected barb cut length and depth. In general, the mandrel device is positioned adjacent to the rotary mount and the monofilament suture is wrapped around the mandrel under tension. The razor rotates/translates around the rotary mount and impinges upon and enters into the suture. The angle at which the razor enters the filament can be set by selecting the angle at which the razor is mounted on the rotary mount. The razor slices into the filament at a predetermined cut angle (relative to a plane tangent to the surface of the filament at the cut location) and penetrates the filament to a predetermined depth, with each such contact of the razor and the suture cutting a barb. The filament is pulled along the curved surface of the mandrel after a first barb has been cut to curve and expose a fresh surface in which a second barb is cut in the same manner. This process continues along a predetermined length of the suture to form the barbed portion of the suture.

Figure 2:
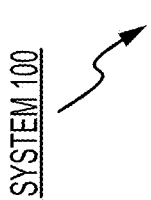
FIG. 2 shows a schematic view of the system of FIG. 1 for manufacturing a barbed suture with the razor mounted to a rotary mount according to various exemplary embodiments.

FIG. 2 shows a schematic view of the system 100 for manufacturing a barbed suture with the razor 104 mounted to a rotary mount 102 according to various exemplary embodiments. The system includes a rotary mount 102 on which the razor 104 is mounted so that the razor 104 can be rotated along a predetermined path.

Figure 3:
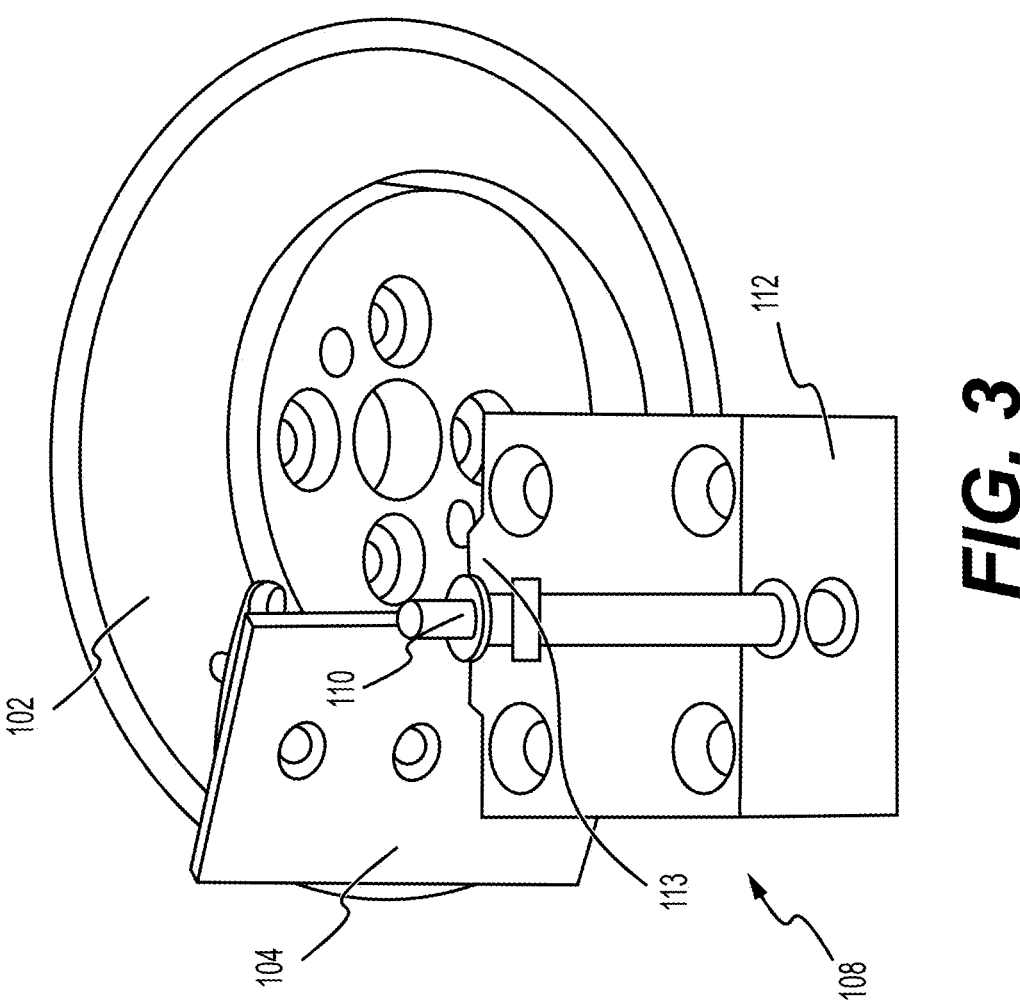
FIG. 3 shows the system of FIG. 1 including the rotary mount and a mandrel device including a mandrel around which a suture filament is curved, with the razor rotating toward the mandrel, according to various exemplary embodiments.
Figure 3:
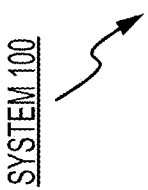

FIG. 3 shows the system 100 including the rotary mount 102 and a mandrel device 108 including a mandrel 110 around which a suture filament is curved, with the razor 104 rotating toward the mandrel 110, according to various exemplary embodiments. The mandrel device 108 can include the mandrel 110 and a fixture 112 to which the mandrel 110 is mounted. A suture filament can be curved around the mandrel 110 (e.g., partially wrapped around the mandrel 110), as shown above in FIG. 1.

In some embodiments, the system includes a filament control system, e.g., a tension control system for the filament, that imparts forces and movement upon the filament in coordination with the operation of the rotary mount. In general, the filament control system is configured to apply an axial tension and/or torsional tension to the filament while advancing the filament around the mandrel. Those skilled in the art understand that different types of control systems may be used. In various exemplary embodiments, the filament control system (e.g., tension control system) can include one or more grasping components for holding the ends of the filament, one or more winding components, e.g., a spool around which the end(s) of the filament can be wound and/or unwound, and/or one or more motors such as, e.g., a servo motor. The filament can be held on its first end (upstream of the mandrel) and its second end (downstream of the mandrel) so that pulling forces can be applied on one or both ends to provide axial tension and to advance the filament around the mandrel. In some embodiments, the filament is wound on one or both ends on a miniature spool and the spool is rotated to advance the filament around the mandrel. In some embodiments, a braking system implemented, e.g., at the spool holder, provides the axial tension to the filament, e.g., by imparting drag to the filament. In some embodiments, the filament is supported on each end by a respective device that provides a controlled pulling force to the filament—e.g., a first device upstream from the mandrel and a second device downstream from the mandrel. It is noted that the filament can be twisted during the above-described processing such that an arcuate (e.g., spiral or helical) path can be imparted to the filament so that successive barbs are cut along this path that winds around the circumference of the filament. Accordingly, the control system can also provide torsional tension to the filament. In some embodiments, after the barbed portion of the suture is cut, the filament is then cut free from the spool downstream of the mandrel in a final step. This allows for fully automated manufacture of multiple barbed sutures.

In some embodiments, the system includes features for enabling razor cutting with high precision. In some embodiments, the mandrel fixture includes surfaces against which the filament is held, e.g., surfaces 113 as shown above in FIGS. 1 and 3. This ensures that the suture filament 114 does not deviate from a desired path around the mandrel 110 as the filament travels around the mandrel 110, particularly after a cut has been applied to the filament and the internal stress profile of the filament at the cut location and the surrounding area changes dramatically. In some embodiments, the axial and torsional tension applied to the filament ensures that the filament is kept in intimate contact with the mandrel without overstretching. It is noted that this arrangement ensures that other means for maintaining the correct position of the filament may be dispensed with (e.g., are not required). For example, other systems for maintaining a desired position of the filament on the mandrel have included forming a groove or slot in the mandrel in which the filament is to be carried. As would be understood by those skilled in the art, this and other techniques may be eliminated from systems according to the disclosed embodiments. This arrangement further enables precision cutting despite any small imperfections that may be present in system components, e.g., a mandrel that is not perfectly cylindrical. In some embodiments, the devices holding the ends of the suture include dancer arms that mitigate the effects of such small imperfections.

In some embodiments, the tension control system described above can pull the filament along the mandrel in coordination with the rotating razor so that the razor makes cuts at desired intervals along the filament. In some embodiments, the razor continuously rotates at a set rate and the filament is progressed around the mandrel at a rate that ensures a desired portion of filament is exposed to the cutting edge. In some embodiments, the filament continuously progresses around the mandrel. In other embodiments, the filament proceeds in a stepwise manner as would be understood by those skilled in the art.

In some embodiments, no additional processing steps are required as the cut barbs naturally lift away from the central (longitudinal) axis of the filament to a desired height. In this context, lifting generally refers to the rotation of the barbs beyond the shadow profile of the suture after the cut has been made. This process may occur naturally after the razor cut. It should be understood that the radius of curvature of the cut surface of the filament and the cut surface forming the barb would be naturally equivalent upon initial cut, however, the barb may subsequently curve to a greater degree, e.g., due to internal forces, causing the radius of curvature of the cut surface of the barb to be less than the radius of curvature of the cut surface of the filament and further causing the tip of the barb to rise relative to the filament. The degree of this natural curvature depends, for example, on the material of the filament, thickness of the barbs (e.g., the cut depth) and other characteristics of the barb and/or the filament as would be understood by those skilled in the art.

In some embodiments, after cutting on the small diameter mandrel, if no further process steps are taken, the barb may elastically return to a position near the cut path, resulting in a minimal barb height dimension. In other words, the arcuate cut shape of the sequence of barbs will be formed, but the barb will not necessarily exhibit a substantial barb height. This may occur for certain filament materials and barb shapes. In these cases, to produce a barb with a more substantial height, a mechanical or thermal process may be incorporated and used in conjunction with the barb cutting on the small diameter mandrel to further raise the barbs away from the uncut portions of the surface of the filament.

In some embodiments, the height of the barbs is adjusted after the barb is cut by a mechanical and/or thermal lifting process. The methods of barb formation described herein are readily adjustable to achieve a range of barb lengths and heights depending on design goals such as tissue holding strength and passage force, e.g., maximizing the tissue holding strength while maintaining a relatively low passage force and/or minimizing the passage force while maintaining a relatively high holding strength.

In some exemplary embodiments, the longer barbs are adjusted in height, rotated further out of alignment with the longitudinal axis of the suture, i.e., "lifted" to a height extending significantly beyond the outline of the suture filament. In one aspect, a lifting process comprises a mechanical lifter in-line with the razor cutting process.

Figure 4:
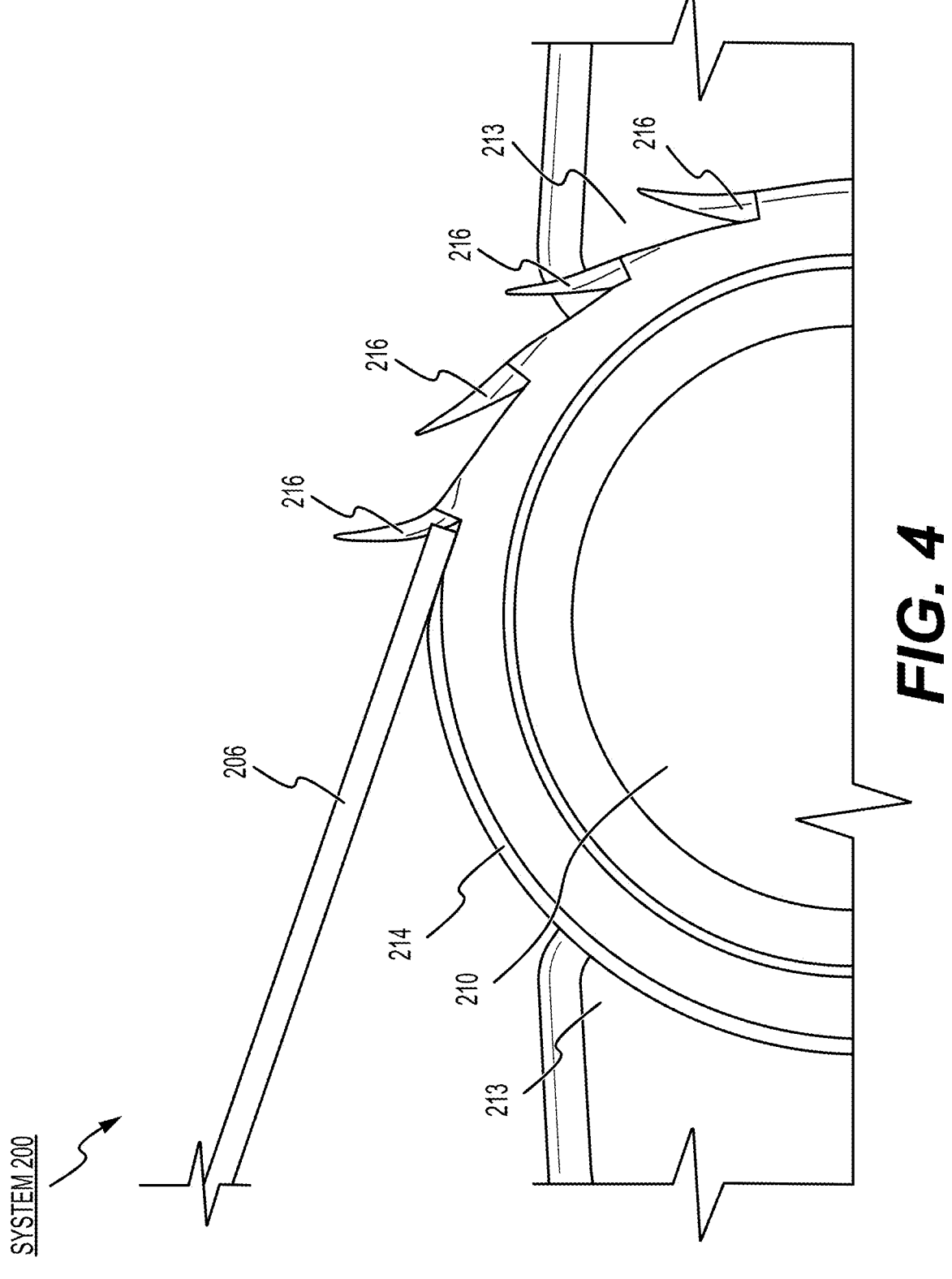
FIG. 4 shows a system including a barb lifter striking barbs cut into a suture filament to adjust the barb height according to various exemplary embodiments.

FIG. 4 shows a system 200 including a barb lifter 206 striking barbs 216 cut into a suture filament 214 to adjust the barb height according to various exemplary embodiments.

The barb lifter 206 can be made to impinge on a newly cut barb 216 in a manner that pushes the barb 216 forward (along the longitudinal axis of the filament from the point at which a razor 204 entered the filament toward the far end of the cut). The barb lifter 206 plastically deforms the polymer near the barb base (i.e., the point at which the cut defining the barb ends). In this way, the barb tip is permanently shifted or lifted to exhibit a barb height further extended above the filament body. The path of the barb lifter 206 of this embodiment is substantially the same as the path of the razor 204 used to make the barb cut, i.e., these components impinge on the filament 214 at the same angle.

The shape of the barb lifter 206 can be similar to that of the razor 204, or can be any other shape (whether planar or curved in nature) that allows the edge of the barb lifter 206 to engage with and plastically deform the newly cut barb 216 while the suture filament 214 is still in contact with the mandrel 210 (i.e., mounted to the mandrel 210 under tension). The barb lifter 206 can be made from a variety of materials including polymers and metals as would be understood by those skilled in the art. The thickness of the barb lifter 206 should not be substantially greater than the filament diameter to permit the barb lifter 206 to engage the barb 216 in a manner that causes plastic deformation and lifting of the barb 216. Thinner barb lifters may elastically deform and thereby slide along the filament for a distance before catching and pushing the barb 116 near its base.

Figure 5:
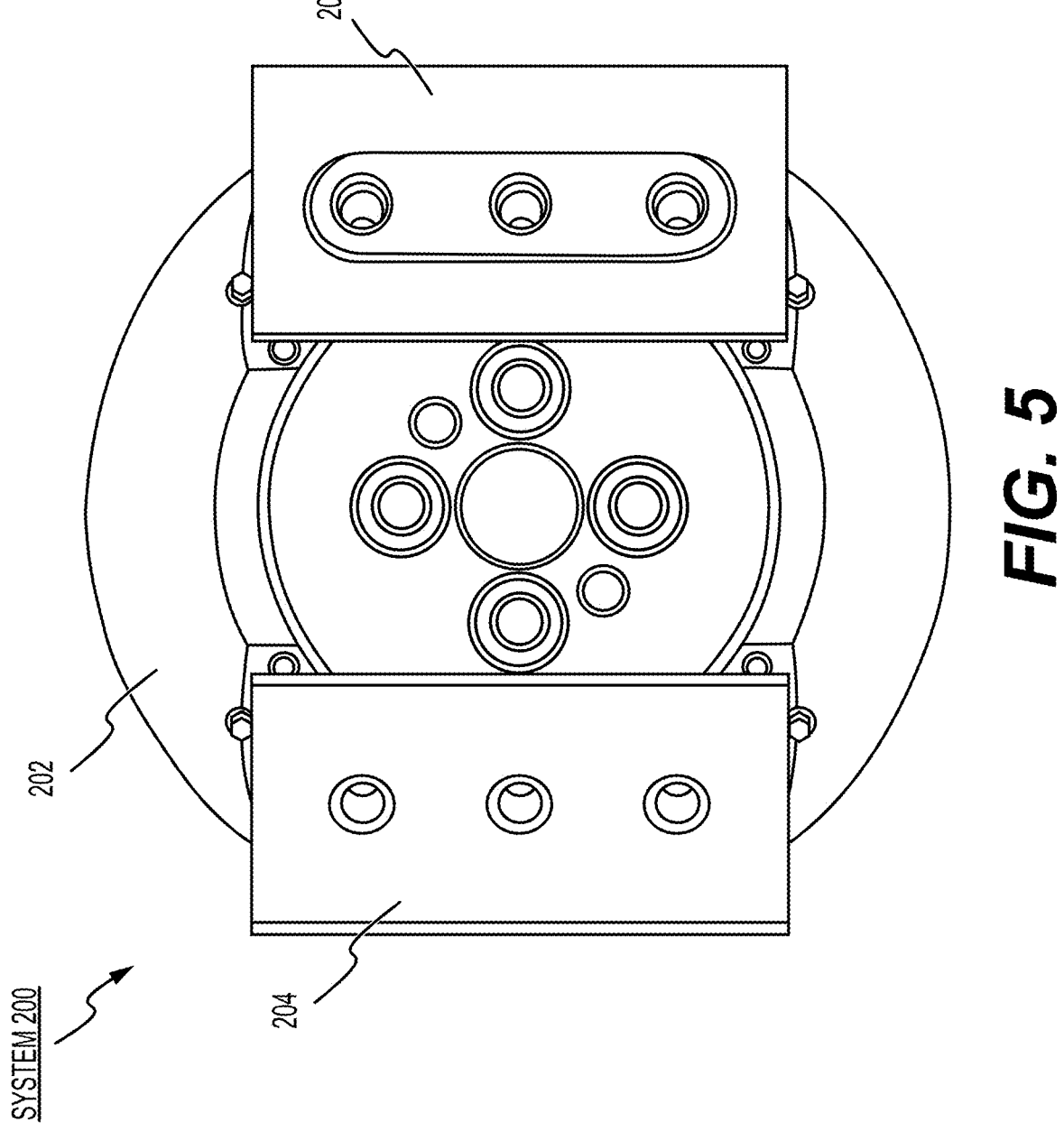
FIG. 5 shows a schematic view of the system of FIG. 4 for manufacturing a barbed suture with a razor and a barb lifter mounted to a rotary mount according to various exemplary embodiments.

FIG. 5 shows a schematic view of the system 200 for manufacturing a barbed suture with a razor 204 and a barb lifter 206 mounted to a rotary mount 202 according to various exemplary embodiments. The system includes a rotary mount 202 on which the razor 204 and the barb lifter 206 are mounted. The razor 204 is used for barb cutting and the barb lifter 206 is used to achieve a desired barb height.

Figure 6:
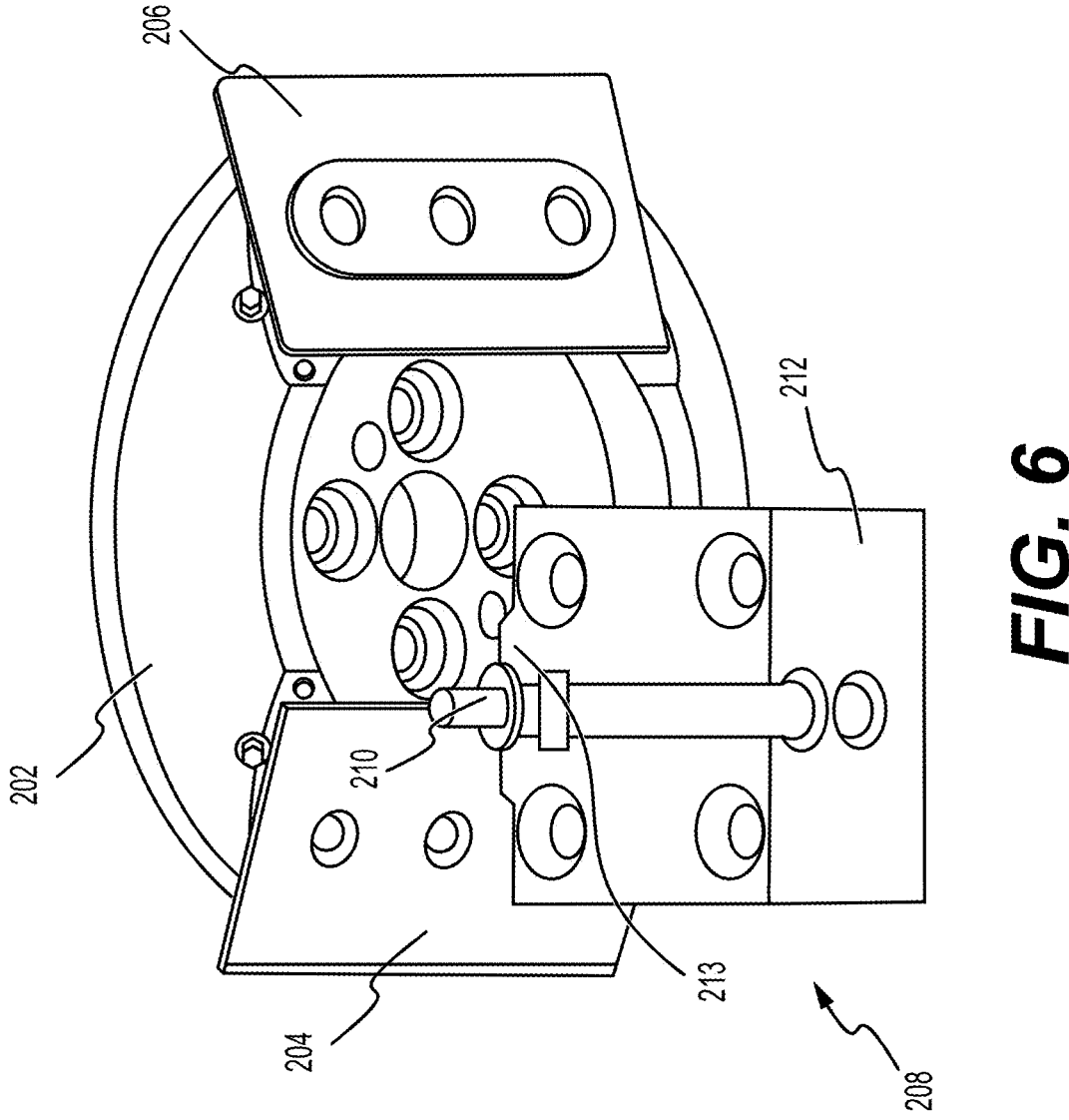
FIG. 6 shows the system of FIG. 4 including the rotary mount and a mandrel device including a mandrel around which a suture filament is curved, with the razor rotating toward the mandrel, according to various exemplary embodiments.
Figure 6:

The razor 204 and the barb lifter 206 of this exemplary embodiment are rotated around the rotary mount 202 and a mandrel device 208 is positioned adjacent to the rotary mount 202 and oriented such that the razor 204 and the barb lifter 206 can be brought into impinging contact with a suture filament mounted to the mandrel 210 to form the barbs 116 in the suture filament 114, as shown in FIG. 6 below.

In this example, the razor 204 and the barb lifter 206 are positioned opposite one another on the circumference of the rotary mount 202 (i.e., separated from one another by 180 degrees). However, other orientations may suffice or even provide process benefits. For example, the razor 204 and barb lifter 206 can be positioned along the circumference of the rotary mount at an offset of 90 degrees relative to one another, allowing sufficient room to pattern two razors and two lifters on a single rotary mount.

FIG. 6 shows the system 200 including the rotary mount 202 and a mandrel device 208 including a mandrel 210 around which a filament is curved, with the razor 204 rotating toward the mandrel 210, according to various exemplary embodiments. The mandrel device 208 can include the mandrel 210 and a fixture 212 to which the mandrel 210 is mounted. A suture filament can be mounted to the mandrel 210, as shown above in FIG. 4.

Figure 7:
FIG. 7 shows the system of FIG. 6 with the barb lifter rotating toward the mandrel around which the suture filament is curved according to various exemplary embodiments.

FIG. 7 shows the system 200 with the barb lifter 206 rotating toward the mandrel 210 around which a suture filament is curved according to various exemplary embodiments. As the rotary mount 202 continues rotating, the barb lifter 206 can be made to impinge upon the newly cut barb 216 in a manner that pushes the barb 216 forward and functions to plastically deform the polymer near the barb base. The path of rotation of the barb lifter 206 of this embodiment is the same as the path of the razor 204 used to make the barb cut.

In these embodiments, when the barb lifter is used in-line with the razor, it must be ensured that the barb lifter can engage and lift the cut barb. If the mandrel diameter is too large, the preliminary cut angle of the barb (made at the filament circumference) will be small, producing a weak mal-formed barb tip. By using a fine diameter mandrel, a robust barb tip can be produced while cutting a barb that is long enough for the barb lifter to engage from the back side and lift, producing the desired combination of barb height, length and barb tip robustness.

In some embodiments, by using a smaller diameter mandrel, e.g., 1.5 mm, the barbs may be made to overlap along the length of the filament. This design can be produced by matching the projected barb cut length to the barb spacing while the filament is curved around the small diameter mandrel. While on the mandrel, the circumferential regions of the curved filament are in a state of tension. As the filament transitions off the mandrel and straightens, residual tensile stresses are relieved and the material around the barb's contracts forcing the tip of each barb to overlap the base of the neighboring barb by a modest distance.

This overlapping barb structure can help the barb engage with the surrounding tissue thereby improving the per barb tissue holding strength while reducing the distance for barbs to engage with surrounding tissue (e.g., reduced tissue slack when applied tension is released). As such, a lesser degree of barb lifting may be required to achieve a desired tissue holding effect.

In other embodiments, the system includes components such as a heat source for adjusting the height of the barbs in a thermal process. In these embodiments, the lifting process comprises the application of thermal conditions that cause the barbs to rise radially away from remaining portions of the filament. In some embodiments, a thermal barb lifting process is used after the razor cutting process has been completed. Certain polymer filaments (e.g., those that exhibit a relatively low modulus of elasticity) may be more difficult to process to achieve a significant barb height via mechanical lifting alone. However, thermal processes may be used in place of or in addition to mechanical barb lifting to increase the barb height.

As previously described, a fine diameter mandrel may be used to produce barbs with significant length and limited cut depth. The suture may then be subject to a thermal process which causes the barbs to deflect outwards producing the desired barb height. In some embodiments, a rapid thermal in-line annealing step is used in which the filament is exposed to a specific temperature for a specific duration of time. This process has been demonstrated, for example, with MONOCRYL* filament in which the razor cut filament was exposed to ~120° C. for 15 seconds. Thus, this process may be used for a suture according to the present invention by exposing the filament into which the barbs have been cut to ~120° C. for 15 seconds while holding the ends of the filament under tension. In another embodiment, the filament is exposed to ~125° C. for 12 seconds. Those skilled in the art may anticipate that temperatures in the range of 110 to 130° C. for durations ranging from 60 to 5 seconds may be similarly effective. Thus, this process may be used for a suture according to the present invention to raise the temperature of the filament into which the barbs have been cut while holding the ends of the filament under tension. Different specific temperature/time is required for other filament materials such as PDS* which may require a lower filament temperature than MONOCRYL* to achieve barb deflection/height.

Since the filament starts with a high degree of uniform molecular orientation, entropic forces drive the filament to contract as the temperature is increased. However, as the filament is constrained at both ends during this inline processing, only the material near the free surfaces of the cut barbs can contract while the molecular orientation and desirable material properties in the suture core are maintained. The heat source may then be removed while the filament is cooled under tension to lock in the new barb height.

Off-line batch processes may also be used for longer or shorter anneal periods to achieve similar effects. Rapid radiative heat transfer processes may be adopted to more effectively heat the surface regions of the filament to a higher temperature than the core of the filament. In this way, the microstructure at the core of the filament and corresponding tensile properties may be more effectively retained. As would be understood by those skilled in the art, dyed sutures often show increased absorption of IR radiation at short depths and, thus, may be more suitable for rapid thermal processing via radiative heat transfer processes. To optimize process speed and retention of filament core properties, thermal processing using laser light (especially from IR frequency diode lasers) may be used.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A system for manufacturing a monofilament barbed suture, comprising:
   a rotary mount configured to rotate about a central axis;
   a razor mounted to the rotary mount; and
   a mandrel device positioned adjacent to the rotary mount, the mandrel device comprising a mandrel mounted to a fixture, the mandrel configured to support a filament on a curved surface of the mandrel so that, as the razor rotates with the rotary mount, an edge of the razor impinges upon an exterior surface of the filament to impart a linear cut to the filament to a cut depth within the filament to form a barb,
   a filament control system to which a first end of the filament upstream from the mandrel and a second end of the filament downstream from the mandrel are coupled,
   wherein the filament control system is configured to pull the first end of the filament and the second end of the filament to provide axial tension to the filament,
   wherein the axial tension brings the filament into contact with the curved surface of the mandrel; and
   wherein the mandrel comprises a diameter of 4 millimeters or less.

2. The system of claim 1, wherein the curved surface of the mandrel having the diameter of 4 millimeters or less is configured to impart a curvature to the filament so that the linear cut into the filament by the razor results in a cut surface of the filament that, upon transitioning off the curved surface of the mandrel, exhibits a continuous curve, the cut surface extending from a first end at the exterior surface of the filament to a second end at the cut depth, and wherein a first angle of a first tangent of the cut surface at the first end is greater than a second angle of a second tangent of the cut surface at the second end relative to a longitudinal axis of the filament.

3. The system of claim 2, wherein the mandrel device is oriented so that a cut path of the razor imparts the linear cut into the filament such that the first angle of the first tangent of the cut surface at the first end is greater than 15 degrees relative to the longitudinal axis of the filament.

4. The system of claim 2, wherein the mandrel device is oriented so that the cut path of the razor imparts the linear cut into the filament such that the second angle of the second tangent of the cut surface at the second end, upon transitioning off the curved surface of the mandrel, is less than 5 degrees.

5. The system of claim 1, wherein the filament control system includes a spool around which the filament is wound and a braking system imparting the axial tension to the filament, wherein the spool is rotated to wind the filament and translate the filament along the curved surface of the mandrel so that, upon a subsequent rotation of the razor around the rotary mount, a further linear cut is imparted to a portion of the filament adjacent to the linear cut.

6. The system of claim 5, wherein the rotary mount rotates at a set velocity and the filament control system translates the filament along the curved surface of the mandrel a predetermined distance per rotation of the rotary mount to form a series of barbs along a length of the filament.

7. The system of claim 6, wherein translating the filament along the curved surface of the mandrel is performed continuously while the series of barbs is formed.

8. The system of claim 6, wherein translating the filament along the curved surface of the mandrel is performed in steps and, during each linear cut, the filament is not translating along the curved surface of the mandrel.

9. The system of claim 1, wherein the fixture of the mandrel device includes a first surface against which a first portion of the filament upstream from the linear cut is held and a second surface against which a second portion of the filament downstream from the linear cut is held, the first and second surfaces providing forces to impede uncontrolled motion of the filament during barb cutting.

10. The system of claim 1, wherein a ratio of mandrel diameter to filament diameter is greater than 3 and less than 25.

11. A system for manufacturing a monofilament barbed suture, comprising:
   a rotary mount configured to rotate about a central axis;
   a razor mounted to the rotary mount;
   a mandrel device positioned adjacent to the rotary mount, the mandrel device comprising a mandrel mounted to a fixture, the mandrel configured to support a filament on a curved surface of the mandrel so that, as the razor rotates with the rotary mount, an edge of the razor impinges upon an exterior surface of the filament to impart a linear cut to the filament to a cut depth within the filament to form a barb, wherein the mandrel comprises a diameter of 4 millimeters or less; and
   a mechanical barb lifter mounted to the rotary mount,
   wherein the barb lifter is configured to rotate with the rotary mount to impinge upon a cut side of the barb to increase a height of the barb relative to the filament, and
   wherein the barb lifter impinging upon the cut side of the barb plastically deforms the barb so that the height of the barb is maintained.

12. The system of claim 11, wherein the razor is mounted to the rotary mount at a first position opposing a second position of the barb lifter.

13. A system for manufacturing a monofilament barbed suture, comprising:

a rotary mount configured to rotate about a central axis;

a razor mounted to the rotary mount;

a mandrel device positioned adjacent to the rotary mount, the mandrel device comprising a mandrel mounted to a fixture, the mandrel configured to support a filament on a curved surface of the mandrel so that, as the razor rotates with the rotary mount, an edge of the razor impinges upon an exterior surface of the filament to impart a linear cut to the filament to a cut depth within the filament to form a barb, wherein the mandrel comprises a diameter of 4 millimeters or less; and a heat source configured to provide a set temperature to a cut barb for a set duration to cause the barb to deflect radially outwards to increase a height of the barb relative to the filament.

14. The system of claim 13, wherein the heat source is configured to be applied when the filament is under axial tension.

* * * * *